United States Patent [19]

Lindner et al.

[11] Patent Number: 5,256,631

[45] Date of Patent: Oct. 26, 1993

[54] SUBSTITUTED 1,2,4-TRIAZINEDIONES, AND THEIR USE

[75] Inventors: Werner Lindner, Köln; Axel Haberkorn, Wuppertal, both of Fed. Rep. of Germany

[73] Assignee: Bayer Aktiengesellschaft, Leverkusen, Fed. Rep. of Germany

[21] Appl. No.: 822,482

[22] Filed: Jan. 17, 1992

[30] Foreign Application Priority Data

Jun. 19, 1991 [DE] Fed. Rep. of Germany ....... 4120138

[51] Int. Cl.$^5$ ............... C07D 253/707; C07D 253/06; A01N 43/707
[52] U.S. Cl. .................................. 504/229; 544/182
[58] Field of Search ................... 544/182; 71/93; 504/229

[56] References Cited

U.S. PATENT DOCUMENTS

| | | | |
|---|---|---|---|
| 3,883,528 | 5/1975 | Mylari | 544/182 |
| 3,912,723 | 10/1975 | Miller | 544/182 |
| 4,956,004 | 9/1990 | Theodoridis | 504/229 |

FOREIGN PATENT DOCUMENTS

| | | |
|---|---|---|
| 0232932 | 8/1987 | European Pat. Off. . |
| 0383285 | 8/1990 | European Pat. Off. . |
| 2149645 | 9/1972 | Fed. Rep. of Germany . |
| 2423972 | 1/1975 | Fed. Rep. of Germany . |
| 2722537 | 11/1978 | Fed. Rep. of Germany . |
| 3408924 | 9/1985 | Fed. Rep. of Germany . |
| 3531919 | 3/1987 | Fed. Rep. of Germany . |
| 3904593 | 8/1990 | Fed. Rep. of Germany . |

OTHER PUBLICATIONS

Chemical Abstracts, vol. 91, Nov. 5, 1979, No. 19 entry 157771d.

*Primary Examiner*—John M. Ford
*Attorney, Agent, or Firm*—Sprung Horn Kramer & Woods

[57] ABSTRACT

The present invention relates to new substituted 1,2,4-triazinediones of the formula (I)

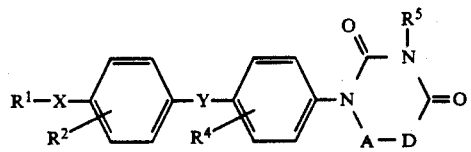

A—D represents —N=CH— or

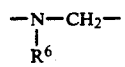

X represents O or S,
Y represents O, S, CO,

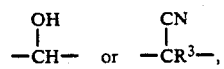

$R^1$ represents $C_{1-4}$-halogenoalkyl,
$R^2$ represents hydrogen, halogen or $C_{1-4}$-halogenoalkyl,
$R^3$ represents hydrogen or $C_{1-4}$-alkyl,
$R^4$ represents hydrogen, halogen, halogenoalkyl or $C_{1-4}$-alkyl, and
$R^5$ and $R^6$ represent hydrogen, $C_{1-4}$-alkyl, halogenoalkyl, aralkyl or alkinyl, to processes for their preparation, intermediates for carrying out the process and their use as antiprotozoal agents.

8 Claims, No Drawings

SUBSTITUTED 1,2,4-TRIAZINEDIONES, AND THEIR USE

The present invention relates to new substituted 1,2,4-triazinediones, to processes for their preparation, to intermediates for carrying out this process, and to their use for controlling parasitic protozoa and in particular coccidia and fish parasites.

The use of substituted 1,2,4-triazinediones for controlling coccidia is known. However, the reaction of these compounds is not satisfactory in every case.

The present invention relates to

1. New compounds of the formula (I)

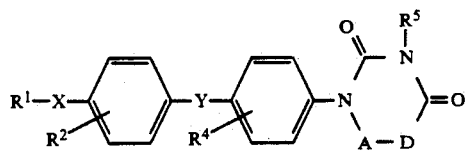

in which
A—D represents —N=CH— or

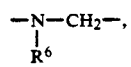

X represents O or S, SO or $SO_2$,
Y represents O, S, CO,

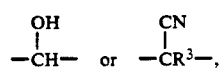

$R^1$ represents $C_{1-4}$-halogenoalkyl,
$R^2$ represents hydrogen, halogen or $C_{1-4}$-halogenoalkyl,
$R^3$ represents hydrogen or $C_{1-4}$-alkyl,
$R^4$ represents one or more identical or different radicals from the series consisting of hydrogen, halogen, halogenoalkyl and $C_{1-4}$-alkyl, and
$R^5$ and $R^6$, independently of one another, represent hydrogen, $C_{1-4}$-alkyl, halogenoalkyl, aralkyl or alkinyl.

2. Process for the preparation of the new compounds of the formula (I) according to (1), characterised in that in the cases in which A–D represents —N=CH—, a) in the case in which $R^5$ represents a radical other than hydrogen, compounds of the formula (Ia)

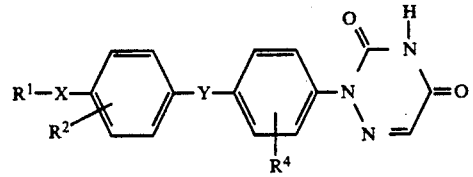

in which
Y, X, $R^1$, $R^2$, $R^3$ and $R^4$ have the meaning indicated in (1),
are reacted with compounds of the formula (II)

$R^5$-B (II)

in which $R^5$ represents optionally substituted alkyl, alkenyl, alkinyl or aralkyl and
B represents halogen, —O—$SO_2$-alkyl, —O—$SO_2$-aryl or —O—$SO_2$-halogenoalkyl, or b) in that compounds of the formula (III)

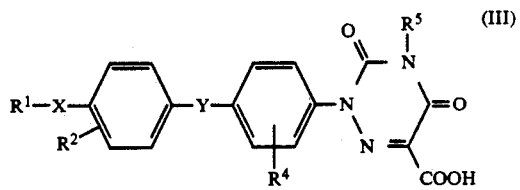

in which
Y, X, $R^1$, $R^2$, $R^3$, $R^4$ and $R^5$ have the meanings indicated in (1),
are decarboxylated by heating, and additionally in that in the cases in which A-D represents

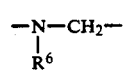

c) compounds of the formula (Ib)

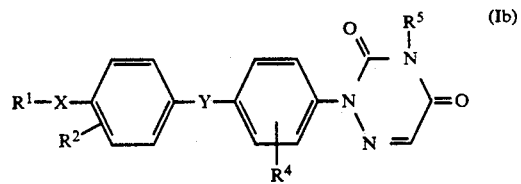

are hydrogenated, or d) in that compounds of the formula

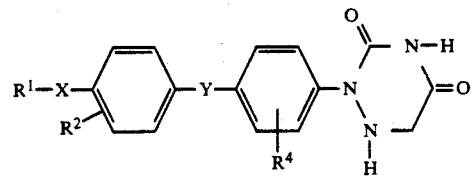

in which
Y, X, $R^1$, $R^2$ and $R^4$ have the abovementioned meaning, are reacted with compounds of the formula II $R^5$-B (II)

in which
$R^5$ represents optionally substituted alkyl, alkenyl, alkinyl or aralkyl and
B represents halogen, —O—$SO_2$-alkyl, —O—$SO_2$-aryl or —O—$SO_2$-halogenoalkyl, or e) in that compounds of the formula

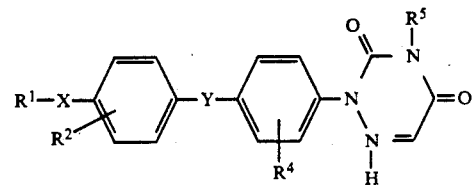

in which

Y, X, $R^1$, $R^2$, $R^4$ and $R^5$ have the abovementioned meaning, but $R^5$ does not represent hydrogen, are reacted with compounds of the formula VI $$R^6\text{-B} \quad \text{(VI)}$$

in which
$R^6$ and B have the abovementioned meaning.

3. New compounds of the formula (III)

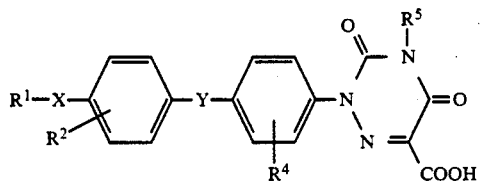

in which
Y, X, $R^1$, $R^2$, $R^3$, $R^4$ and $R^5$ have the meaning indicated in (1).

4. Process for the preparation of the new compounds of the formula (III) according to (3), characterised in that compounds of the formula (IV)

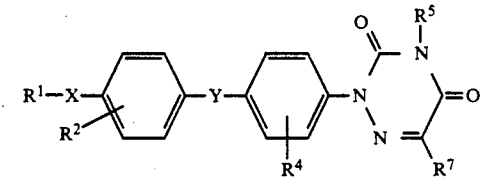

in which
Y, X, $R^1$, $R^2$, $R^3$, $R^4$ and $R^5$ have the meaning indicated in (1),
$R^7$ represents CN or the radical —CO—N($R^5$)—$COOR^8$, and
$R^8$ represents alkyl or aryl, are heated in the presence of aqueous mineral acids.

5. New compounds of the formula (IV)

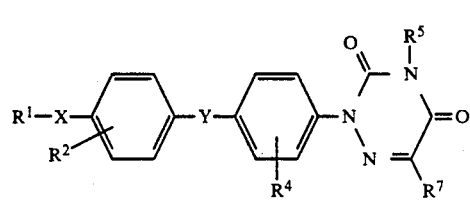

in which

Y, X, $R^1$, $R^2$, $R^3$, $R^4$, $R^5$ and $R^7$ have the meaning indicated in (4).

6. Process for the preparation of the new compounds of the formula (IV) according to (5), characterised in that compounds of the formula (V)

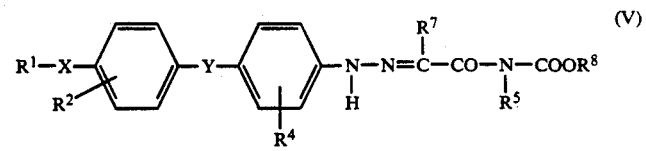

in which
Y, X, $R^1$, $R^2$, $R^3$, $R^4$, $R^5$, $R^7$ and $R^8$ have the meaning indicated in (5),
are heated in the presence of bases.

7. New compounds of the formula (V)

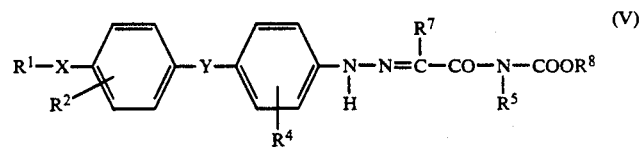

in which
X, $R^1$, $R^2$, $R^3$, $R^4$, $R^5$, $R^7$ and $R^8$ have the meaning indicated in (5) and $R^7$ can additionally represent hydrogen.

8. Process for the preparation of the new compounds of the formula (V), characterised in that compounds of the formula (VI)

in which
Y, X, $R^1$, $R^2$, $R^3$ and $R^4$, have the meaning indicated in (1),
are diazotised in a manner known per se and subsequently reacted with compounds of the formula (VII)

$$\underset{R^5}{CH_2\text{—CO—N—}COOR^8} \overset{R^7}{|} \quad \text{(VII)}$$

in which
$R^5$, $R^7$ and $R^8$ have the meaning indicated in (5).

The compounds of the formula (I) and their salts with bases or acids are outstandingly suitable for the control of parasitic protozoa and in particular of coccidia and fish parasites.

Preferred compounds of the formula (I) are compounds in which
X represents O or S,
Y represents O, S, CO,

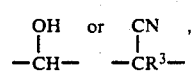

$R^1$ represents $C_{1-4}$-halogenoalkyl, $R^2$ represents hydrogen, halogen or $C_{1-4}$-halogenoalkyl, $R^3$ represents hydrogen or $C_{1-4}$-alkyl, $R^4$ represents one or more identical or different radicals from the series consisting of hydrogen, halogen, halogenoalkyl and $C_{1-4}$-alkyl, and $R^5$ and $R^6$ represent hydrogen.

Particularly preferred compounds of the formula (I) are in which

X represents O or S,

Y represents O, S or

$R^1$ represents $C_{1-4}$-halogenoalkyl, $R^2$ represents hydrogen or halogen, $R^4$ represents one or more identical or different radicals from the series consisting of hydrogen, halogen, $C_{1-4}$-alkyl and trifluoromethyl, and $R^5$ and $R^6$ represent hydrogen.

Very particularly preferred compounds of the formula (I) are those in which

X represents O or S,

Y represents O, S or

$R^1$ represents $C_{1-4}$-halogenoalkyl, in particular trifluoromethyl, $R^2$ represents hydrogen, $R^4$ represents one or more identical or different radicals from the series consisting of hydrogen, fluorine, chlorine and bromine, in particular chlorine, and $R^5$ and $R^6$ represent hydrogen.

The following compounds may be mentioned in detail

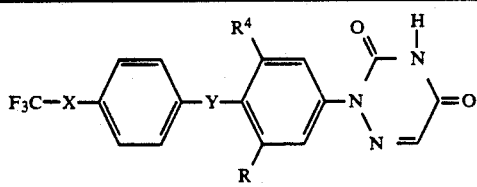

| X | Y | R | $R^4$ |
|---|---|---|---|
| O | O | Cl | Cl |
| S | O | Cl | Cl |
| O | S | Cl | Cl |
| S | S | Cl | Cl |
| O | CHCN | Cl | Cl |
| S | CHCN | Cl | Cl |

The following compounds may furthermore be mentioned

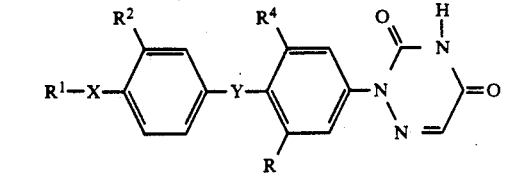

| X | Y | $R^1$ | $R^2$ | R | $R^4$ |
|---|---|---|---|---|---|
| O | O | $CHF_2$ | H | Cl | Cl |
| O | O | $CHF_2$ | Cl | Cl | Cl |
| O | O | $CF_2CHF_2$ | H | Cl | Cl |
| O | O | $CF_2CHF_2$ | Cl | Cl | Cl |
| O | O | $CF_3$ | H | $CH_3$ | $CH_3$ |
| O | S | $CHF_2$ | H | Cl | Cl |
| O | S | $CHF_2$ | Cl | Cl | Cl |
| O | S | $CF_2CHF_2$ | H | Cl | Cl |
| O | S | $CF_2CHF_2$ | Cl | Cl | Cl |
| O | S | $CF_3$ | Cl | $CH_3$ | $CH_3$ |
| O | CHCN | $CHF_2$ | H | Cl | Cl |
| O | CHCN | $CHF_2$ | Cl | Cl | Cl |
| O | CHCN | $CF_2CHF_2$ | H | Cl | Cl |
| O | CHCN | $CF_2CHF_2$ | Cl | Cl | Cl |
| O | CHCN | $CF_3$ | H | $CH_3$ | $CH_3$ |
| S | CHCN | $CF_3$ | H | $CH_3$ | $CH_3$ |
| S | O | $CHF_2$ | H | Cl | Cl |
| S | O | $CF_3$ | H | $CH_3$ | $CH_3$ |
| S | O | $CHF_2$ | Cl | Cl | Cl |
| S | O | $CF_2CHF_2$ | H | Cl | Cl |

If 2-[4-(4'-trifluoromethylthiophenyl)-3,5-dichlorophenoxy]-1,2,4-triazine-3,5-(2H,4H)dione is employed as the compound of the formula (Ia) and methyl iodide is employed as the compound of the formula (II) in process 2a) for the preparation of the compounds of the formula (I), in which $R^5$ does not represent hydrogen, the process can be described by the following equation:

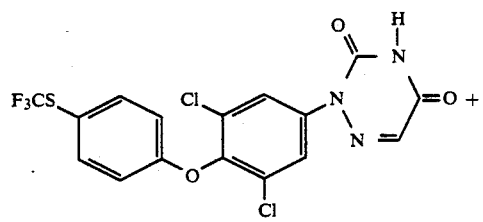

compounds of the formula (Ia) are prepared as described in process 2b).

The compounds of the formula (II) are known or can be prepared by known methods. Methyl iodide and ethyl bromide may be particularly mentioned.

The process is carried out by reacting a compound of the formula (Ia) with compounds of the formula (II) in the presence of a base and of a diluent.

Suitable diluents are virtually all the inert organic solvents. These preferably include aliphatic and aromatic, optionally halogenated hydrocarbons, benzine, ligroin, benzene, toluene, xylene, methylene chloride, ethylene chloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone and also dimethyl sulphoxide, tetramethylene sulphone and hexamethylphosphoric triamide.

The process is carried out in the presence of bases. Preferred bases which may be mentioned are the alkali metal hydroxides such as sodium hydroxide, alkali metal alkoxides such as sodium methoxide or potassium-butoxide, metal hydrides such as sodium hydride or organic bases such as 1,8-diazabicyclo[5.40]undec-7-ene (DBU).

The process is carried out at normal pressure and at temperatures between 20° and 140° C.

The reaction is carried out by combining equimolar amounts of the compound of the formula (Ia) and base, adding an equimolar amount of the compound of the formula (II) to this mixture and heating to the reaction temperature.

Both the compounds of the formula (I) and the compounds of the formula (Ia) can be prepared by process 2b) described below.

If 2-[4-(4'-trifluoromethylphenoxy)-1,2,4-triazine-2,5(2H,4H)dione-6-carboxylic acid is employed as the compound of the formula VIII in process 2b) for the preparation of the compounds of the formula II, the can be described by the following equation:

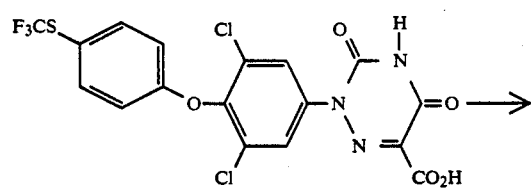

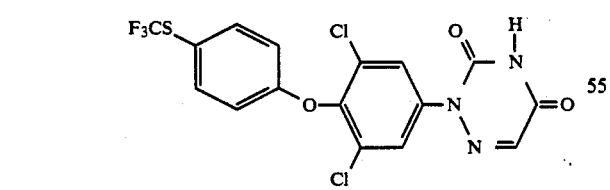

The compounds of the formula (III) are prepared by the process described further below (4). Compounds of the formula (III) are preferably employed in which Y, X, $R^1$, $R^2$, $R^3$, $R^4$ and $R^5$ have the preferred meanings indicated for the compounds of the formula (I).

Individual compounds of the formula (III) which may be mentioned are

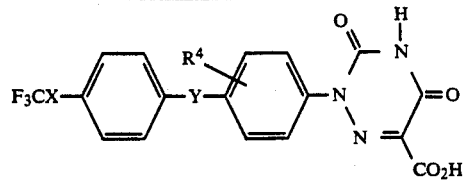

| X | Y | $R^4$ |
|---|---|---|
| O | O | 3,5-Cl$_2$ |
| S | O | 3,5-Cl$_2$ |
| O | S | 3,5-Cl$_2$ |
| S | S | 3,5-Cl$_2$ |
| O | CHCN | 3,5-Cl$_2$ |
| S | CHCN | 3,5-Cl$_2$ |

The decarboxylation is optionally carried out in the presence of inert organic diluents These include aliphatic and aromatic, optionally halogenated hydrocarbons such as nonane, decane, dodecane or xylenes, alcohols such as diethylene glycol, ethers such as ethylene glycol monobutyl ether or diethylene glycol dibutyl ether, sulphoxides such as dimethyl sulphoxide and sulphones such as tetramethylene sulphone.

The reaction can moreover be carried out in the presence of mercapto group-containing carboxylic acids such as, for example, mercaptoacetic acid or thiosalicylic acid.

The reaction is carried out at temperatures between 150° and 300° C., if appropriate in the presence of mercapto group-containing carboxylic acids such as, for example, mercaptoacetic acid, preferably between 160° and 250° C., in particular between 180° and 210° C.

The reaction is carried out at normal pressure. The compounds of the formulae (III) are heated in substance or dissolved or suspended in the respective diluent.

If 2-[4-(4'-trifluoromethylthiophenyl)-3,5-dichlorophenoxy]-1,2,4-triazine-3,5-[2H,4H)dione is employed as the compound of the formula Ib in process 2c, the process can be described by the following equation:

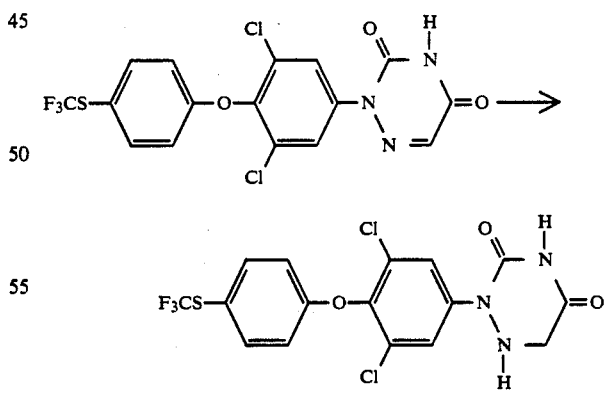

The compounds of the formula Ib are new and are obtained, for example, by the processes 2a–c).

Compounds of the formula Ib may preferably be mentioned in which X, Y, $R^1$, $R^2$, $R^3$, $R^4$ and $R^5$ have the preferred meanings mentioned for the compounds of the formula I.

In particular, the following compounds of the formula Ib may be mentioned:

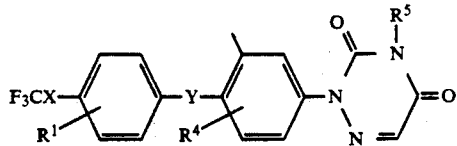

| X | Y | R¹ | R⁴ |
|---|---|---|---|
| O | O | Cl | Cl |
| S | O | Cl | Cl |
| O | S | Cl | Cl |
| S | S | Cl | Cl |
| O | CHCN | Cl | Cl |
| S | CHCN | Cl | Cl |
| SO₂ | CHCN | Cl | Cl |

Process 2c) is carried out by heating a compound of the formula Ib in the presence of a reducing agent and of an acid. Reducing agents which can be used are metals such as, for example, zinc and metal salts such as, for example, tin(II) chloride, metal hydrides such as lithium aluminium hydride and catalytically activated hydrogen.

Acids employed are dilute mineral acids such as, for example, hydrochloric acid and organic acids such as, for example, glacial acetic acid. The reaction can optionally be carried out in the presence of a diluent. Diluents which can be used as inert organic solvents. These include hydrocarbons such as, for example, toluene, ethers such as, for example, dioxane, ketones such as, for example, acetone and alcohols such as, for example, ethanol. The reduction is carried out at temperatures between 80° and 120° C. at normal pressure or at elevated pressure.

Processes 2d and 2e are carried out according to the conditions indicated for process 2a.

If 2-[4-(4'-trifluoromethylthiophenyl-3,5-dichlorophenoxy)]-6-cyano-1,2,4-triazine-3,5(2H,4H)dione is employed as the compound of the formula (IV) in process 4 for the preparation of the compounds of the formula (III), the process can be described by the following equation:

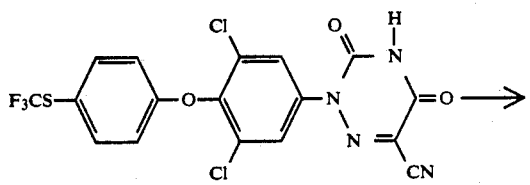

The compounds of the formula (IV) are new. They are prepared by the process described under (6).

Compounds of the formula (IV) are preferably employed in which Y, X, $R^1$, $R^2$, $R^3$, $R^4$ and $R^5$ has the preferred meanings indicated for the compounds of the formula (I) and $R^7$ represents CN.

Hydrolysis of the compounds of the formula (VI) is carried out under acidic conditions. Acids used are mineral acids such as, for example, hydrochloric acid, hydrobromic acid, sulphuric acid and mixtures of mineral acids and organic acids such as, for example acetic acid or propionic acid.

The reaction is carried out at temperatures between 80° and 120° C. It is carried out under normal pressure.

The compounds of the formula (IV) are dissolved in 10–30 times the volume of the acid or of the acid mixture and the mixture is heated until hydrolysis is complete.

If ethyl N-[[[cyano(3,5-dichloro-(4'-trifluoromethylphenyl)phenoxy-hydrazinylidene]methyl]carbonyl]-carbamate is employed as the compound of the formula XI in process 6 for the preparation of the compounds of the formula (IV), the process can be described by the following equation:

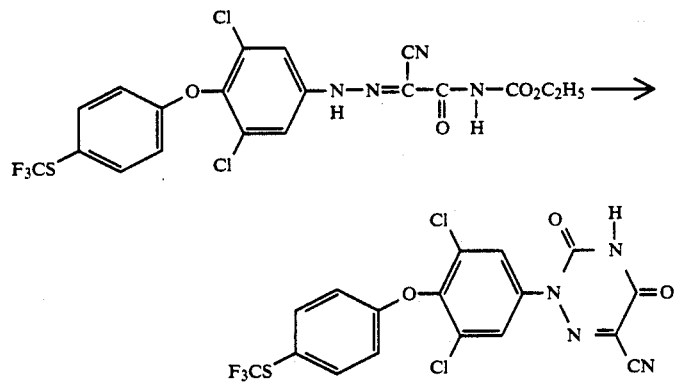

The compounds of the formula (V) are new. They are prepared by the process described under (8). Compounds of the formula (V) are preferably employed in which Y, X, $R^1$, $R^2$, $R^3$, $R^4$ and $R^5$ have the preferred meanings indicated for the compounds of the formula (I), $R^8$ represents $C_{1-4}$-alkyl, in particular methyl or ethyl and phenyl, and $R^7$ represents CN.

Individual compounds of the formula (V) which may be mentioned are

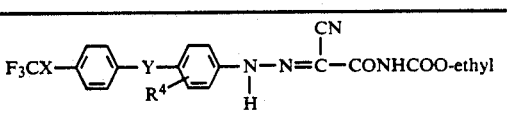

| X | Y | R⁴ |
|---|---|---|
| O | O | 3,5-Cl₂ |
| S | O | 3,5-Cl₂ |

-continued

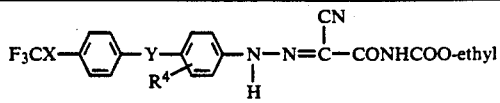

| X | Y | R⁴ |
|---|---|---|
| O | S | 3,5-Cl$_2$ |
| S | S | 3,5-Cl$_2$ |
| O | CHCN | 3,5-Cl$_2$ |
| S | CHCN | 3,5-Cl$_2$ |

Process 6) is Carried out by heating a compound of the formula (V), if appropriate in the presence of a solvent and of a base.

Solvents and bases used are the solvents and bases mentioned for the preparation of the compounds I. Further particularly preferred organic solvents employed are alcohols such as, for example, ethanol or organic acids such as, for example, glacial acetic acid.

Particularly preferred bases are the hydroxides and acetates of the alkali metals or alkaline earth metals such as, for example, NaOH or sodium acetate and potassium acetate.

The reaction is carried out under normal pressure at temperatures between 70° and 150° C., preferably between 70° and 100° C.

The base used is employed in a 10–80% molar excess. The reaction mixture is preferably acidified using a dilute mineral acid such as, for example, hydrochloric acid after cyclisation is complete and the product obtained as a solid is filtered off.

The compounds of the formula VIII employed in process 6) are new. They are prepared by the process described under (8).

If 4-(4'-trifluoromethylthiophenyl-3,5-dichloroaniline is employed as the compound of the formula (VI) and ethyl cyanoacetylurethane is employed as the compound of the formula (VII) in process 8) for the preparation of the compounds of the formula (V), the process can be described by the following equation:

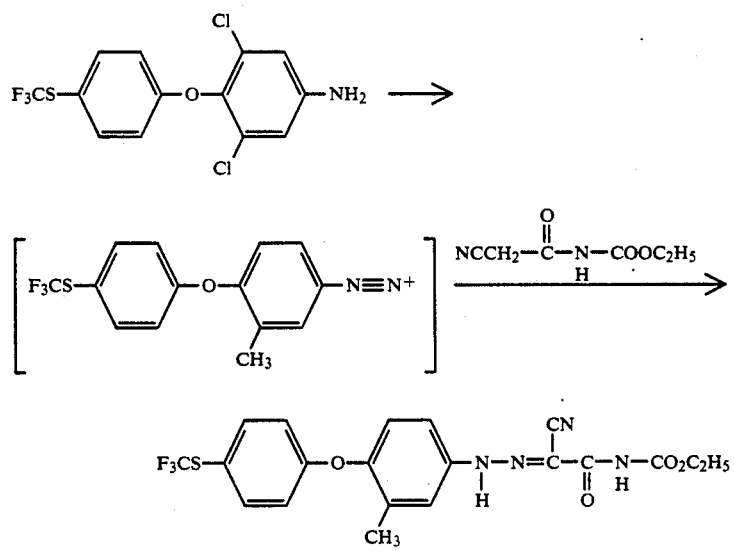

The compounds of the formulae (VI) and (VII) are known or can be prepared analogously to known processes (cf. DE-OS (German Published Specification) 2,413,722; 2,718,799; US. Pat. No. 4,005,218; Le A 26 382).

The process is carried out by reacting an aniline of the formula (VI) with NaNO$_2$ and conc. mineral acid such as, for example, HCl, if appropriate in the presence of a diluent.

Diluents used are the water-miscible diluents such as alcohols, for example methanol, ethanol, glycol ethers such as monomethylglycol ether, nitriles such as acetonitrile, dimethyl sulphoxide, organic acids such as, for example, glacial acetic acid, formic acid or propionic acid, or mixtures of organic acids, preferably a mixture of glacial acetic acid and propionic acid.

The diazonium salt generated in this way is reacted in situ with a compound of the formula (VII) such as, for example, malonydiurethane or cyanoacetylurethane in the presence of a base. Bases used are hydroxides and carbonates of the alkali metals and alkaline earth metals and acetates of sodium, potassium and ammonium.

Organic bases such as pyridine or triethylamine can additionally be used.

Diazotisation is carried out at normal pressure and at temperatures between 0° C. and 10° C. The addition of the compounds of the formula (VII) is carried out at 0° to 20° C. Aniline and nitrite are reacted in equimolar amounts in an excess of acid which is preferably 2–3 times the molar amount. The CH-acid compound is added in a 0 to 30% molar excess, preferably a 10% excess. The base is added in a 1.5–2.5 times molar excess. Advantageously, a reverse addition can also be carried out, i.e. the diazonium salt of the compound of the formula (VI) generated by diazotisation is added dropwise at 0° to 10° C. to a mixture of a compound of the formula (VII) and the respective solvent or solvent mixture.

The coupling product of the diazonium salt and CH-acid compound is insoluble in the reaction medium and can be isolated as a solid.

The process can also be carried out such that compounds of the formula (VI) are formed directly without isolation of the compound of the formula (V). To do this, the diazotisation of the anilines of the formula (VI) and the reaction with the urethanes of the formula (VII) is carried out in a diluent suitable for the cyclisation. The reaction mixture is heated after diazotisation and coupling have been carried out and the triazinedione of the formula (IV) is then isolated.

Diluents which may be mentioned are: alcohols such as methanol and ethanol.

For cyclisation, the reaction mixture is heated to about 80° to 120° C., preferably about 80° to 100° C.

Working-up is carried out as indicated further above for process (6) for the preparation of the compounds of the formula (IV).

The active compounds are suitable for combating parasitic protozoa which are encountered in the keeping and raising of animals with productive, breeding, zoo, laboratory, experimental and pet animals, and have favourable toxicity to warm-blooded animals. They are active against all or individual stages of development of the pests and against resistant and normally sensitive strains. By combating the parasitic protozoa, disease, cases of death and yield reductions (for example in the production of meat, milk, wool, hides, eggs, honey etc.) should be reduced so that more economical and simpler keeping of animals is possible through the use of the active compounds.

The parasitic protozoa include:

Mastigophora (Flagellata) such as, for example, Trypanosomatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example *Giardia lamblia* and *G. canis*.

Sarcomastigophora (Rhizopoda) such as Entamoebidae, for example *Entamoeba histolytica*, Hartmanellidae, for example *Acanthamoeba sp.* and *Hartmanella sp.*

Apicomplexa (Sporozoa) such as Eimeridae, for example *Eimeria acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. dabliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna. E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. Zurenii, Globidium spec., Isospora belli, I. canis, I. felis, I. ohioensis, I. rivolta, I. spec., I. suis, Cystisospora spec., Cryptosporidium spec.* such as Toxoplasmadidae, for example *Toxoplasma gondii*, such as Sarcocystidae, for example *Sarcocystis bovicanis, S. bovihominis, S. ovicanis, S. ovifelis, S. spec., S. suihominis* such as Leucozoidae, for example *Leucozytozoon simondi*, such as Plasmodiidae, for example *Plasmodium berghei, P. falciparum, P. malariae, P. ovale, P. vivax, P. spec.*, such as Piroplasmea, for example *Babesia argentina, B. bovis, B. canis, B. spec., Theileria parva, Theileria spec.*, such as Adeleina, for example *Hepatozoon canis, H. spec.*

In addition Myxospora and Microspora, for example *Glugea spec.* and *Nosema spec.*

In addition *Pneumocystis carinii* and Ciliophora (Ciliata) such as, for example, *Balantidium coli, Ichthiophthirius spec., Trichodina spec.* and *Epistylis spec.*

The compounds according to the invention are also active against protozoa which occur as parasites in insects. Those which may be mentioned are parasites of the Microsporida strain, in particular the genus Nosema. *Nosema apis* in the honey bee may be particularly mentioned.

The productive and breeding animals include mammals such as, for example, cattle, horses, sheep, pigs, goats, camels, water buffalo, donkeys, rabbits, fallow deer, reindeer, animals having a valuable coat such as, for example, mink, chinchilla, racoons, birds such as, for example, hens, geese, turkeys, ducks, doves, and species of bird for keeping at home and in the zoo. In addition, productive and ornamental fish are included.

The laboratory and experimental animals include mice, rats, guinea pigs, golden hamsters, dogs and cats.

The pet animals include dogs and cats.

The fish include productive, breeding, aquarium and ornamental fish of all ages which live in fresh and salt water. The productive and breeding fish include, for example, carp, eel, trout, whitefish, salmon, bream, roach, rudd, chub, sole, plaice, halibut, Japanese yellowtail (*Seriola quinqueradiata*), Japanese eel (*Anguilla japonica*), red seabream (*Pagurus major*), sea bass (*Dicentrarchus labrax*), grey mullet (*Mugilus cephalus*), pompano, gilthread seabream (*Sparus auratus*), Tilapia spp., chichlidae species such as, for example, Plagioscion or Channel catfish. The agents according to the invention are particularly suitable for the treatment of fry for example carp of 2-4 cm body length. The agents are also very highly suitable in the feeding of eels.

Administration can be carried out both prophylactically and therapeutically.

The administration of the active compounds is carried out directly or enterally, parenterally, dermally or nasally in the form of suitable preparations.

Enteral administration of the active compounds is carried out, for example, orally in the form of powders, suppositories, tablets, capsules, pastes, drinks, granules, drenches, boli, medicated feed or drinking water. Dermal administration is carried out, for example, in the form of dipping, spraying, bathing, washing, pouring-on and spotting-on and powdering. Parenteral administration is carried out, for example, in the form of injection (intramuscular, subcutaneous, intravenous, intraperitoneal) or by implants.

Suitable preparations are:

solutions such as injection solutions, oral solutions, concentrates for oral administration after dilution, solutions for use on the skin or in body cavities, pouring-on formulations and gels;

emulsions and suspensions for oral or dermal administration and also for injection; semi-solid preparations;

formulations in which the active compound is processed in an ointment base or in an oil-in-water or water-in-oil emulsion base;

solid preparations such as powders, premixes or concentrates, granules, pellets, tablets, boli, capsules; aerosols and inhalants, and moulded articles containing active compound.

Injection solutions are administered intravenously, intramuscularly and subcutaneously.

Injection solutions are produced by dissolving the active compound in a suitable solvent and, if necessary, adding additives such as solubilisers, acids, bases, buffer salts, antioxidants and preservatives. The solutions are sterile filtered and bottled.

Solvents which may be mentioned are: physiologically tolerable solvents such as water, alcohols such as ethanol, butanol, benzyl alcohol, glycerol, hydrocarbons, propylene glycol, polyethylene glycols, N-methylpyrrolidone, and mixtures of these.

The active compounds may optionally also be dissolved in physiologically tolerable vegetable or synthetic oils which are suitable for injection.

Solubilisers which may be mentioned are: solvents which promote the solution of the active compound in the main solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are administered directly. Concentrates are administered orally after previously diluting to the administration concentration. Oral solutions and concentrates are prepared as described above for the injection solutions, it being possible to dispense with sterile working.

Solutions for use on the skin are poured on dropwise, spread on, rubbed in, sprinkled on, sprayed on or applied by dipping, bathing or washing. These solutions are prepared as described above for the injection solutions.

It may be advantageous to add thickeners during the preparation. Thickeners are: inorganic thickeners such as bentonites, colloidal silica, aluminium monostearate, organic thickeners such as cellulose derivatives, polyvinyl alcohols and their copolymers, acrylates and metacrylates.

Gels are applied to or spread on the skin or introduced into body cavities. Gels are prepared by adding such a quantity of thickener to solutions which have been prepared as described for the injection solutions that a clear composition having an ointment-like consistency results. The thickeners indicated above are employed as thickeners.

Pouring-on formulations are poured onto or sprinkled onto limited areas of the skin, whereupon the active compound either penetrates the skin and acts systemically or is distributed on the body surface.

Pouring-on formulations are prepared by dissolving, suspending or emulsifying the active compound in suitable skin-compatible solvents or solvent mixtures. If appropriate, further auxiliaries such as colorants, absorption-promoting substances, antioxidants, light screens and adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone and 2-dimethyl-4-oxy-methylene-1,3-dioxolane.

Colorants are all colorants which may be dissolved or suspended and which are permitted for administration to animals.

Absorption-promoting substances are, for example, DMSO, spreading oils such as isopropyl myristate, dipropylene glycol pelargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Light screens are, for example, substances of the benzophenone class or novantisolic acid.

Adhesives are, for example, cellulose derivatives, starch derivatives, polyacrylates, and natural polymers such as alginates and gelatin.

Emulsions may be administered orally, dermally or as injections.

Emulsions are either of the water-in-oil type or the oil-in-water type.

They are prepared by dissolving the active compound either in the hydrophobic or the hydrophilic phase and homogenising this with the solvent of the other phase with the aid of suitable emulsifiers and, if appropriate, further auxiliaries such as colorants, absorption-promoting substances, preservatives, antioxidants, light screens and viscosity-increasing substances.

Hydrophobic phases (oils) which may be mentioned are: paraffin oils, silicone oils, natural vegetable oils such as sesame oil, almond oil, castor oil, synthetic triglycerides such as caprylic/capric acid biglyceride, triglyceride mixture with vegetable fatty acids of chain length $C_{2-12}$ or other specially selected natural fatty acids, partial glyceride mixtures of saturated or unsaturated fatty acids possibly also containing hydroxyl groups, and mono- and diglycerides of $C_8C_{10}$-fatty acids.

Fatty acid esters such as ethyl stearate, di-n-butyryl adipate, hexyl laurate, dipropylene glycol pelargonate, esters of a branched fatty acid of medium chain length containing saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, inter alia fatty alcohols such as isotridecyl alcohol, 2-octyldodecanol, cetyl stearyl alcohol and oleyl alcohol.

Fatty acids such as, for example, oleic acid and its mixtures.

Hydrophilic phases which may be mentioned are: water, alcohols such as, for example, propylene glycol, glycerol, sorbitol and their mixtures.

Emulsifiers which may be mentioned are: non-ionic surfactants, for example polyoxyethylated castor oil, polyoxyethylated sorbitan monooleate, sorbitan monostearate, glycerol monostearate, polyoxyethyl stearate and alkylphenol polyglycol ethers;

ampholytic surfactants such as di-Na N-lauryl-β-iminodipropionate or lecithin;

anionic surfactants, such as Na lauryl sulphate, fatty alcohol ether sulphates, mono/dialkyl polyglycol ether orthophosphoric acid ester monoethanolamine salt;

cationic surfactants such as cetyltrimethylammonium chloride.

Other auxiliaries which may be mentioned are: substances increasing viscosity and stabilising the emulsion such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions may be administered orally, dermally or as an injection. They are prepared by suspending the active compound in an excipient liquid, if appropriate with the addition of other auxiliaries such as wetting agents, colorants, absorption-promoting substances, preservatives, antioxidants light screens.

Excipient liquids which may be mentioned are all homogeneous solvents and solvent mixtures.

Wetting agents (dispersants) which may be mentioned are the surfactants indicated above.

Other auxiliaries which may be mentioned are those indicated above.

Semi-solid preparations can be administered orally or dermally. They differ from the suspensions and emulsions described above only by their higher viscosity.

In order to prepare solid preparations, the active compound is mixed with suitable excipients, if appropriate with the addition of auxiliaries, and brought into the desired form.

Excipients which may be mentioned are all physiologically tolerable solid inert substances. Those used are inorganic and organic substances. Inorganic substances are, for example, sodium chloride, carbonates such as calcium carbonate, hydrogen carbonates, aluminium oxides, silicic acids, aluminas, precipitated or colloidal silica and phosphates.

Organic substances are, for example, sugars, cellulose, foodstuffs and feeds such as milk powder, animal meal, cereal meal and shreds, and starches.

Auxiliaries are preservatives, antioxidants and colorants which have already been mentioned above.

Other suitable auxiliaries are lubricants and glidants such as, for example, magnesium stearate, stearic acid, talc, bentonites, disintegration-promoting substances such as starch or crosslinked polyvinylpyrrolidone, binders such as, for example, starch, gelatin or linear polyvinylpyrrolidone and dry binders such as microcrystalline cellulose.

The active compounds may also be present in the preparations as a mixture with synergists or with other active compounds.

Ready-to-use preparations contain the active compound in concentrations of 10 ppm-20 per cent by weight, preferably from 0.1-10 per cent by weight.

Preparations which are diluted before use contain the active compound in concentrations of 0.5-90 per cent by weight, preferably from 1 to 50 per cent by weight.

In general, it has proved advantageous to administer amounts of about 0.5 to about 50 mg, preferably 1 to 20 mg, of active compound per kg of body weight per day to attain effective results The active compounds can also be administered together with the feed or drinking water of the animals.

Feeds and foodstuffs contain 0.01 to 100 ppm, preferably 0.5 to 50 ppm of the active compound in combination with a suitable edible material.

Such a feed or foodstuff can be used both for healing purposes and for prophylactic purposes.

The preparation of such a feed or foodstuff is carried out by mixing a concentrate or a premix which contains 0.5 to 30%, preferably 1 to 20% by weight, of an active compound in a mixture with an edible organic or inorganic excipient with customary feeds. Edible excipients are, for example, maize flour or maize and soya bean flour or mineral salts which preferably contain a small amount of an edible dust-preventing oil, for example maize oil or soya oil. The premix obtained in this way can then be added to the complete feed before feeding it to the animals.

Use in coccidiosis may be mentioned as an example: For the curing and prophylaxis, for example, of coccidiosis in poultry, in particular in hens, ducks, geese and turkeys, 0.1 to 100 ppm, preferably 0.5 to 100 ppm, of an active compound are mixed with a suitable edible material, for example a nutritious feed. If desired, these amounts can be increased, particularly if the active compound is well tolerated by the recipient. Administration can correspondingly be carried out via the drinking water.

For the treatment of individual animals, for example in the case of the treatment of coccidiosis in mammals or toxoplasmosis, preferably amounts of active compound of 0.5 to 100 mg/kg of body weight are administered daily in order to obtain the desired results. In spite of this it may be periodically necessary to deviate from the amounts mentioned, in particular depending on the body weight of the test animal or the type of administration method, but also on account of the type of animal and its individual reaction to the active compound or the manner of formulation and the time or the interval at which it is administered. Thus, in certain cases it may be sufficient to manage with less than the minimum amount previously mentioned, whereas in other cases the upper limit mentioned must be exceeded. With the administration of larger amounts, it may be expedient to divide these into a number of individual administrations over the course of the day.

The compounds according to the invention are moreover active against various fish parasites which belong to the helminths (worms).

The fish parasites include from the sub-kingdom of the protozoa, species of the Ciliata strain, for example *Ichthyophthirius multifiliis, Chilodonella cyprini, Trichodina spp., Glossatella spp., Epistylis spp.* of the Myxosporidia strain, for example *Myxosoma cerebralis, Myxidium spp., Myxobolus spp., Heneguya spp., Hoferellus spp.,* the Microsporidia class, for example *Glugea spp., Thelohania spp., Pleistophora spp.,* from the plat helminths strain: trematodes; Monogenea, for example *Dactylogyrus spp., Gyrodactylus spp., Pseudodactylogyrus spp., Diplozoon spp.,* cestodes, for example from the groups of the Caryphyllidea (for example *Caryophyllaeus laticeps*), Pseudophyllidea (for example *Diphyllobothrium spp.*), Tetraphyllidea (for example *Phyllobothrium spp.*) and Protocephalida (for example species of the genus Proteocephalus) and from the strain of the Arthropoda, various parasitic crustaceae, in particular from the sub-classes of the Branchiura (fish-lice) and Copepoda (copepods) and the orders of the Isopoda (isopods) and Amphipoda (amphipods).

The treatment of the fish is carried out either orally, for example via the feed or by short-term treatment, "medicinal bath", into which the fish are put and in which they are kept for some time (minutes up to a number of hours), for example when transferring from one breeding pond to the other.

However, temporary or permanent treatment of the living space of the fish (for example entire pool units, aquaria, tanks or ponds), in which the fish are kept, can also be carried out.

The active compound is administered in preparations which are suited to the applications.

The concentration of the active compound in the preparations is 1 ppm to 10 % by weight.

Preferred preparations for short-term treatment in the course of use as a "medicinal bath", for example in the treatment when transferring the fish or for the treatment of the living space (pool treatment) of the fish, are solutions of the active compound in one or more polar solvents which give an alkaline reaction on diluting with water.

For the preparation of these solutions, the active compound is dissolved in a polar, water-soluble solvent which either gives an alkaline reaction or to which is added an alkaline water-soluble substance. The latter is advantageously also dissolved in the solvent, but can also be suspended in the solvent and only dissolved in the water. After addition of the active compound solution, the water should have a pH of 7-10, but preferably a pH of 8-10.

The concentration of the active compound can be in the range from 0.5-50%, but preferably in a range from 1-25%.

Suitable solvents are all water-soluble solvents in which the active compound is soluble at a sufficient concentration and which are physiologically acceptable.

These are ethyl alcohol, isopropyl alcohol, benzyl alcohol, glycerol, propylene, glycol, polyethylene glycols, poly(oxoethylene)-poly(oxypropylene) polymers, basic alcohols such as mono-, di- and triethanolamine, ketones such as acetone or methyl ethyl ketone, esters such as ethyl lactate, in addition N-methylpyrrolidone, dimethylacetamide, dimethylformamide, and in addition dispersants and emulsifiers such as polyoxyethylated castor oil, polyethylene glycol sorbitan monooleate, polyethylene glycol stearate or polyethylene glycol ethers and polyethylene glycol alkylamines.

Bases which may be mentioned for adjusting the alkaline pH are organic bases such as basic amino acids such as L- or, D,L-arginine, L- or D,L-lysine, methylglucosamine, glucosamine, 2-amino-2-hydroxymethyl-propane-1,3-diol and in addition such as N,N,N',N'-tetrakis-(2-hydroxypropyl)ethylenediamine or polyether tetrol based on ethylenediamine (M.W. 480-420), inorganic bases, such as ammonia or sodium carbonate—if appropriate with the addition of water.

The preparations may also contain 0.1 to 20% by weight, preferably 0.1-10% by weight, of other formulation auxiliaries, such as antioxidants, surfactants, suspension stabilisers and thickeners such as, for example, methylcellulose, alginates, polysaccharides, galactomannans and colloidal silicic acid. The addition of colorants, flavouring and builders for animal nutrition is also possible. Even acids which, together with the base initially introduced, form a buffer system or reduce the pH of the solution, can be mentioned here.

The concentration of the active compound during use depends on the type and duration of the treatment, and the age and condition of the treated fish. It is, for example, for a short-term treatment, 2-50 mg of active compound per liter of water, preferably 5-10 mg per liter, for a treatment period of 3-4 hours. For the treatment of young carp, for example, a concentration of 5-10 mg/l and a treatment period of about 1-4 hours are used.

Eels are treated using concentrations of about 5 mg/l for about 4 hours.

For a relatively long treatment period or for continuous treatment, the concentration can be chosen to be correspondingly lower.

For pool treatments, 0.1-5 mg of active compound per liter of water can be used.

Preparations for use as a food additive are, for example, composed as follows:

| a) Active compound of the formula I | 1-10 parts by weight |
|---|---|
| Soya bean protein | 49-90 parts by weight |
| b) Active compound of the formula I | 0.5-10 parts by weight |
| Benzyl alcohol | 0.08-1.4 parts by weight |
| Hydroxypropyl-methyl cellulose | 0-3.5 parts by weight |
| Water | remainder to 100 |

Preparations for use in "medicinal baths" and for pool treatment are, for example, composed and prepared as follows.

| c) | 2.5 g | of active compound of the formula (I) are dissolved in 100 ml of triethanolamine with warming. |
|---|---|---|
| d) | 2.5 g 12.5 g | of active compound of the formula (I) of lactic acid are dissolved in 100 ml of triethanol amine with warming and stirring. |
| e) | 10.0 g | of active compound of the formula (I) is dissolved in 100 ml of monoethanolamine. |
| f) | Active compound of the formula I | 5.0 g |
| | Propylene glycol | 50.0 g |
| | Sodium carbonate | 5.0 g |
| | Water | to 100 ml |
| g) | Active compound of the formula I | 5.0 g |
| | Monoethanolamine | 10 g |
| | N-Methylpyrrolidone | to 100 ml |
| h) | Active compound of the formula I | 2.5 g |
| | Sodium carbonate | 5.0 g |
| | Polyethylene glycol 200 | to 100 ml |

The active compound is dissolved in polyethylene glycol with warming and sodium carbonate is suspended therein.

EXAMPLE A

Cocciodiosis in hens 9 to 11 day-old chicks were infected with 40,000 sporulated oocysts of strongly virulent strains of *Eiveria acervulina, E. maxima* and *E. tenella*, the disease pathogens of intestinal coccidiosis.

From 3 days before infection until 8 days after infection (end of the experiment), active compound was administered mixed in the food of the animals in the concentration indicated.

The number of oocysts in the faeces was determined with the aid of the McMaster chamber (see Engelbrecht and coworkers "Parasitologische Arbeitsmehoden in Medizin und Veterinärmedizin" (Parasitological Working Methods in Medicine and Veterinary Medicine), p. 172, Akademie-Verlag, Berlin (1965)).

Those dopes are regarded as effective which prevent the excretion of oocysts and/or clinical symptoms of coccidiosis including mortality completely or to a great extent. The effective doses are indicated in the following table:

TABLE 1

| | | | Coccidiosis in hens | | |
|---|---|---|---|---|---|
| Example No. | Dose ppm. | Death rate deaf/employed | Oocyst excretion in % in comparison to the treated infected control | Weight increase in % in comparison to the noninfected untreated control | Blood excretion with the faeces |
| untreated infected | | 2/6 | 100 | 35 | heavy |

TABLE 1-continued

| | | | Coccidiosis in hens | | |
|---|---|---|---|---|---|
| Example No. | Dose ppm. | Death rate deaf/employed | Oocyst excretion in % in comparison to the treated infected control | Weight increase in % in comparison to the noninfected untreated control | Blood excretion with the faeces |
| control 3 | 50 | 0/3 | 0 | 100 | none |

Preparation Examples

I Example of process 2a)

EXAMPLE 1

2-[4-(4-Trifluoromethylmercaptophenyl)phenoxy]-3-N-methyl-3-N-methyl-3,5-(2H,4H)-dioxo-1,2,4-triazine

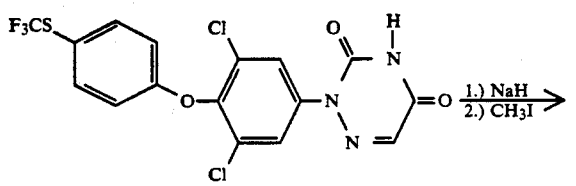

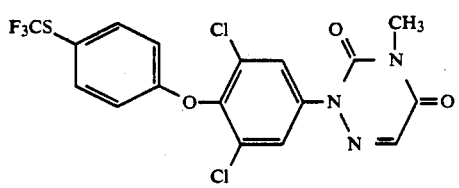

3.1 g (7 mmol) of azauracil are dissolved in 20 ml of absolute DMSO and 0.16 g (6 mmol) of sodium hydride is added. The mixture is stirred at RT for 20 min and 1.5 g (9 mmol) of methyl iodide in 5 ml of DMSO are then added under argon. The reduction mixture is warmed to 50° C. and kept at this temperature for 3 h. It is subsequently concentrated in vacuo and water is then added. After filtering off the precipitated solid with suction, 2.3 g (72% of theory) of the N-methyl compound are obtained.

II Example of process 2b)

EXAMPLE 2

2-[4-(4'-Trifluoromethylmercaptophenyl)-3,5-dichlorophenoxy]-1,2,4-triazine-3,5(2,4)dione

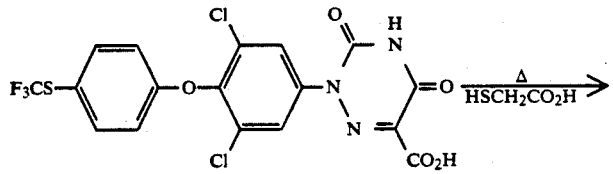

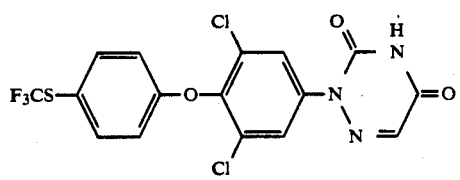

14.8 g (0.03 mol) of carboxylic acid are heated to 170° C. in 20 ml of mercaptoacetic acid. After 1.5 h, the mixture is allowed to cool, water is added and after filtering off 11.5 g (85% of theory) of decarboxylated product are obtained.

The following compounds are prepared analogously

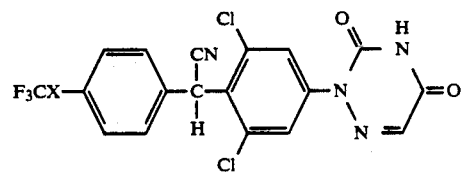

Ex. 3   X = O   m. p. 110° C.

Ex. 4   X = S   m. p. 191° C.

II Example of process 2c)

EXAMPLE 4a 10 g (23 mmol) of 2-[4'-trifluoromethylthiophenyl)-3,5-dichloro-phenoxy]-1,2,4-triazine-3,5(2H, 4H)dione are stirred under reflux for 1.5 h with 10 g of zinc in 100 ml of glacial acetic acid.

The solid is then filtered off hot with suction and the residue is boiled twice with DMF. The filtrates are concentrated stirred with water and the precipitated solid is filtered off with suction. 7.8 g (78% theory) of the dihydro compound are thus obtained as a colourless solid.

The following are prepared analogously

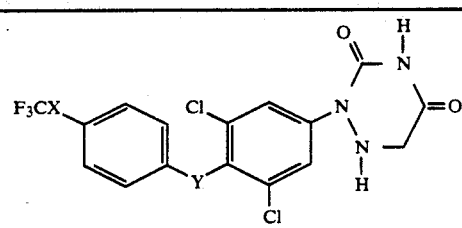

| Ex. No. | X | Y | m.p. |
|---|---|---|---|
| 4b | O | CHCN | |
| 4c | S | CHCN | |

-continued

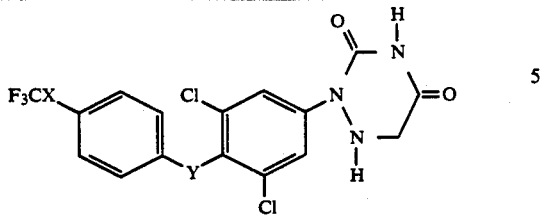

| Ex. No. | X | Y | m.p. |
| --- | --- | --- | --- |
| 4d | S | O | |

III Example of process 4
EXAMPLE 5

2-[4(4'-Trifluoromethylthiophenyl)phenoxy]-3,5-(2H,4H)dioxo-1,2,4-triazine-6-carboxylic acid

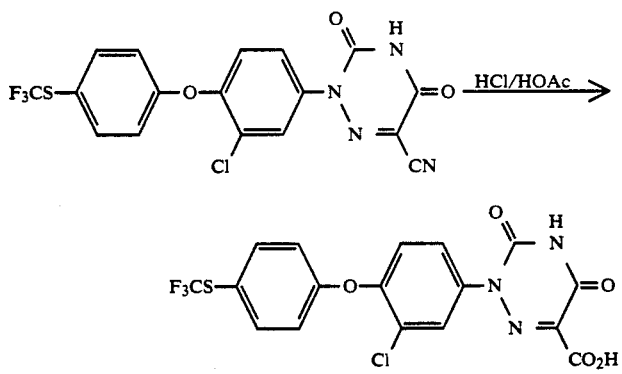

8.5 g (0.02 mol) of cyanoazauracil are boiled in 50 ml of glacial acetic acid and 50 ml of conc. HCl for 4 hours. The mixture is subsequently cooled and diluted with water. The precipitated solid is filtered off with suction and dried. 6.6 g (74%) of the carboxylic acid are thus obtained.

The following compounds are prepared analogously

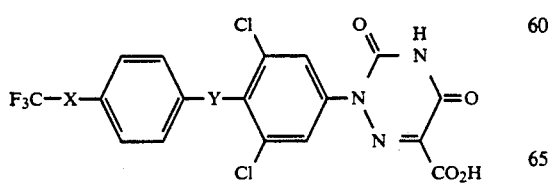

Ex. 6    X = O    Y = CHCN

-continued

Ex. 7    X = S    Y = CHCN

IV Example of process 6
EXAMPLE 8

2-[4-(4'-Trifluoromethylthiophenyl)phenoxy]-3,4-(2H,4),dioxo-6-cyano-1,2,4-triazine

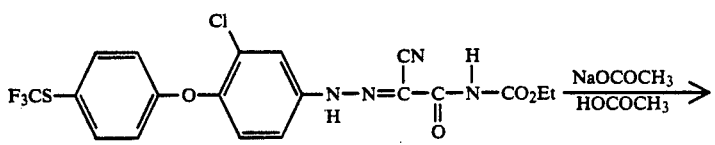

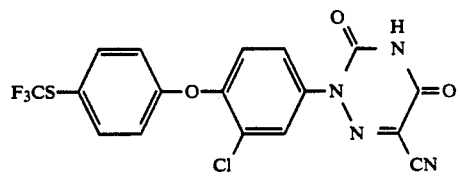

15 g (0.029 mol) of the hydrazonocyanourethane and 3.3 g (0.44 mol) of sodium acetate are heated under reflux in 50 ml of glacial acetic acid for 2 h. The mixture is subsequently cooled and concentrated in vacuo. The residue is stirred with water and the precipitate deposited is filtered off with suction. 10.5 g (83% of theory) of cyanoazauracil are thus obtained after drying.

The following compounds are prepared analogously

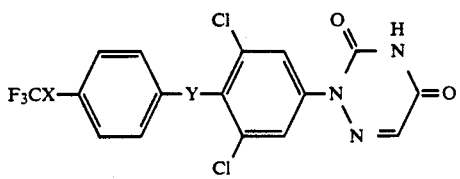

Ex. 9    X = O    Y = CHCN

Ex. 10    X = S    Y = CHCN

V Example of process 7

EXAMPLE 11

Ethyl N-[[[cyano(4-(4'-trifluoromethylthiophenyl)phenoxy)-hydrazinylidene]-methyl]-carbonyl]-carbonate

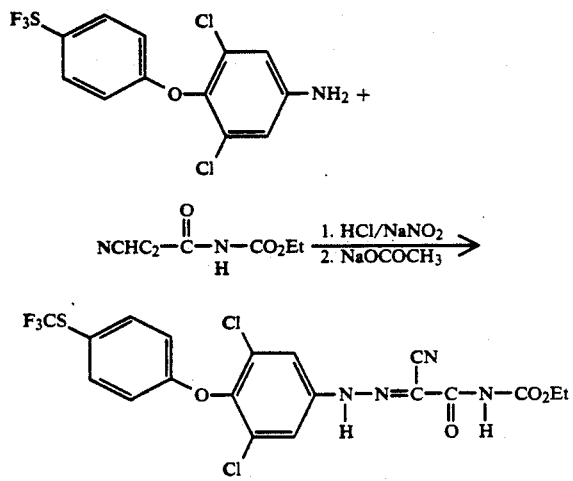

15.8 g (0.045 mol) of aniline are dissolved in 10 ml of conc. HCl and 100 ml of ethanol and a solution of 3.2 g (0.045 mol) of sodium nitrite in 30 ml of water is added dropwise at 0°-5° C. The mixture is subsequently stirred until the solution is clear, then a mixture of 7.1 g (0.045 mol) of cyanoacetylurethane and 11 g (0.13 mol) of sodium acetate is added and the mixture is subsequently stirred at 10° C. for 3 h. The reaction mixture is concentrated in vacuo, stirred with water and the solid is filtered off with suction. 19 g (82%) of product are thus obtained as a finely crystalline yellow powder.

Example of process 8

EXAMPLE 12

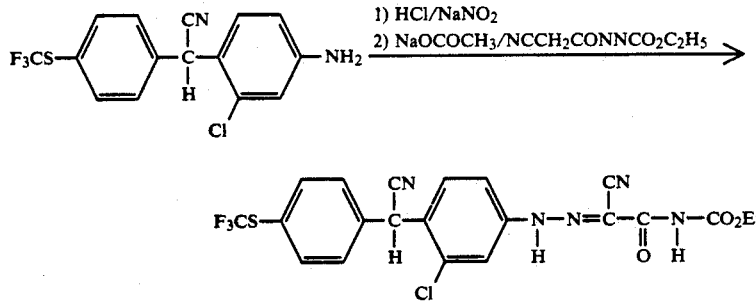

8.9 g (0.026 mol) of aniline are dissolved in 5.6 ml of conc. HCl and a mixture of 50 ml of glacial acetic acid and 50 ml of propionic acid and 1.8 g (0.026 mol) of sodium nitrite are added dropwise at 0° C. in 5 ml of water. The mixture is subsequently stirred for 30 min and the diazonium salt solution thus prepared is added dropwise to a mixture, cooled to 0° C., of 4 g (0.026 mol) of cyanoacetylurethane and 5.3 g (0.065 mol) of sodium acetate in 40 ml of glacial acetic acid and 40 ml of propionic acid and the mixture is subsequently stirred at 10° C. for 3 hours. The reaction mixture is concentrated in vacuo, water is added and the solid is filtered off with suction. 3 g (76%) of the hydrazinyl compound are thus obtained as a yellow solid.

The following compounds are prepared analogously

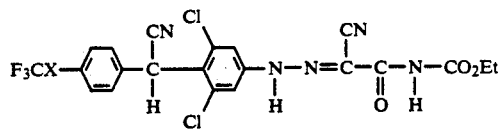

Ex. 13  X = O

Ex. 14  X = S

What is claimed is:

1. A compound selected from compounds of the formula (I)

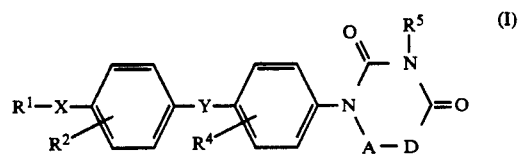

in which

A-D represents —N=CH— or

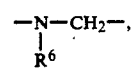

X represents O or S, SO or SO$_2$,

Y represents O, S, CO,

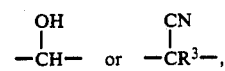

R$^1$ represents C$_{1-4}$-halogenoalkyl,

R$^2$ represents hydrogen, halogen or C$_{1-4}$-halogenoalkyl,

R$^3$ represents hydrogen or C$_{1-4}$-alkyl,

R$^4$ represents one or more identical or different radicals selected from the group consisting of hydrogen, halogen, halogen-C$_{1-4}$-alkyl and C$_{1-4}$-alkyl, and R$^5$ and R$^6$, independently of one another, represent hydrogen, C$_{1-4}$-alkyl, halogen-C$_{1-4}$-alkyl, or phenyl-C$_{1-4}$-alkyl or lower alkinyl.

2. A compound according to claim 1 in which X represents O or S, and R$^5$ and R$^6$ represent hydrogen.

3. A compound according to claim 1, in which X represents O or S,

Y represents O, S or

R¹ represents $C_{1-4}$-halogenalkyl,
R² represents hydrogen or halogen,
R⁴ represents one or more identical or different radicals from the group consisting of hydrogen, halogen, $C_{1-4}$-alkyl and trifluoromethyl, and
R⁵ and R⁶ represent hydrogen.

4. A compound according to claim 1, in which
X represents O or S,
Y represents O, S or

R¹ represents trifluoromethyl,
R² represents hydrogen,
R⁴ represents one or more identical or different radicals from the group consisting of hydrogen, fluorine, chlorine and bromine and
R⁵ and R⁶ represent hydrogen.

5. A compound according to claim 1, wherein such compound is 2-[4-(4'-trifluoromethoxyphenyl-cyanomethyl)-3,5-dichlorophenoxy]-1,2,4-triazine-3,5(2,4)-dione of the formula

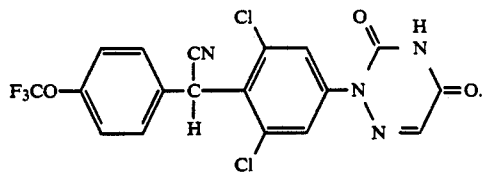

6. A composition active against parasitic protozoa comprising an amount effective therefor of a compound according to claim 1 and a diluent.

7. A method of combating parasitic protozoa which comprises applying to such protozoa or to their habitat an effective amount of a compound according to claim 1.

8. A method of combating parasitic protozoa which comprises applying to such protozoa or to their habitat an effective amount of a compound according to claim 5.

* * * * *

UNITED STATES PATENT AND TRADEMARK OFFICE
CERTIFICATE OF CORRECTION

PATENT NO. : 5,256,631
DATED : October 26, 1993
INVENTOR(S) : Lindner, et al.

It is certified that error appears in the above-indentified patent and that said Letters Patent is hereby corrected as shown below:

Col. 27, line 7    Delete " $C_{1-4}$-halogenalkyl " and substitute -- $C_{1-4}$-halogenoalkyl --

Signed and Sealed this

Twenty-fifth Day of April, 1995

Attest:

BRUCE LEHMAN

Attesting Officer     Commissioner of Patents and Trademarks